United States Patent [19]

Freeman et al.

[11] Patent Number: 4,793,337
[45] Date of Patent: Dec. 27, 1988

[54] ADHESIVE STRUCTURE AND PRODUCTS INCLUDING SAME

[75] Inventors: Frank Freeman, Lawrenceville, N.J.; Michael J. Amery, Upper Makefield Township, Bucks County, Pa.; Clyde L. Sharik, Trenton, N.J.

[73] Assignee: E. R. Squibb & Sons, Inc., Princeton, N.J.

[21] Appl. No.: 931,501

[22] Filed: Nov. 17, 1986

[51] Int. Cl.$^4$ ............................................. A61L 15/00
[52] U.S. Cl. .................... 128/156; 128/155; 428/284; 428/370; 604/368
[58] Field of Search ............ 128/155, 156, 165; 604/368, 897; 427/2; 428/284, 370

[56] References Cited

U.S. PATENT DOCUMENTS

| | | | |
|---|---|---|---|
| 3,122,142 | 2/1964 | Crowe, Jr. ........................... | 128/156 |
| 3,347,236 | 10/1967 | Torr et al. .......................... | 604/368 |
| 3,824,997 | 7/1974 | Franklin et al. ..................... | 128/156 |
| 4,103,062 | 7/1978 | Aberson et al. ..................... | 604/368 |
| 4,253,460 | 3/1981 | Chen et al. ......................... | 128/283 |
| 4,292,972 | 10/1981 | Pawelchak et al. .................. | 128/296 |
| 4,302,500 | 11/1981 | Flora ................................. | 428/284 |
| 4,373,519 | 2/1983 | Errede et al. ....................... | 128/156 |
| 4,421,583 | 12/1983 | Aldred et al. ....................... | 156/167 |
| 4,427,737 | 1/1984 | Cilento et al. ...................... | 524/22 |
| 4,538,603 | 9/1985 | Pawelchak et al. .................. | 128/156 |
| 4,551,490 | 11/1985 | Doyle et al. ........................ | 524/22 |
| 4,562,110 | 12/1985 | Tong ................................. | 428/284 |

FOREIGN PATENT DOCUMENTS 653341 5/1951 United Kingdom .
1283399 7/1972 United Kingdom .
1394741 5/1975 United Kingdom .

OTHER PUBLICATIONS

Thomas, S.; "Use of a Calcium Alginate Dressing" (citation forthcoming).
Cair, Ltd., Product Introduction on Kaltostat, Oct., 1985.
Cair, Ltd., Product Information booklet on Kaltostat.
Kelco, Division of Merck and Co., Inc., first 5 sections of Technical Bulletin on Kelset (pp. 1-15).

Primary Examiner—Richard J. Apley
Assistant Examiner—Paul Prebilic
Attorney, Agent, or Firm—Lawrence S. Levinson; Theodore R. Furman, Jr.

[57] ABSTRACT

In accordance with the present invention an improved adhesive structure for adhesion of an article to a fluid-emitting wound and the surrounding normal skin is disclosed. The adhesive structure comprises a first contact region comprised of a fluid-interactive adhesive material which provides adhesion to the wound and surrounding normal skin; a second contact region comprised of the same or a different adhesive material, which provides adhesion between the first region, or another region integral with the first region, and the article; and, an absorbent region comprised of an absorbent fibrous, fabric or foam material intermediate the first and second regions whereby enhanced cohesion between the first and second regions and between the second region and the article, under conditions of heavy fluid emission, is provided.

17 Claims, 1 Drawing Sheet

U.S. Patent
Dec. 27, 1988
4,793,337
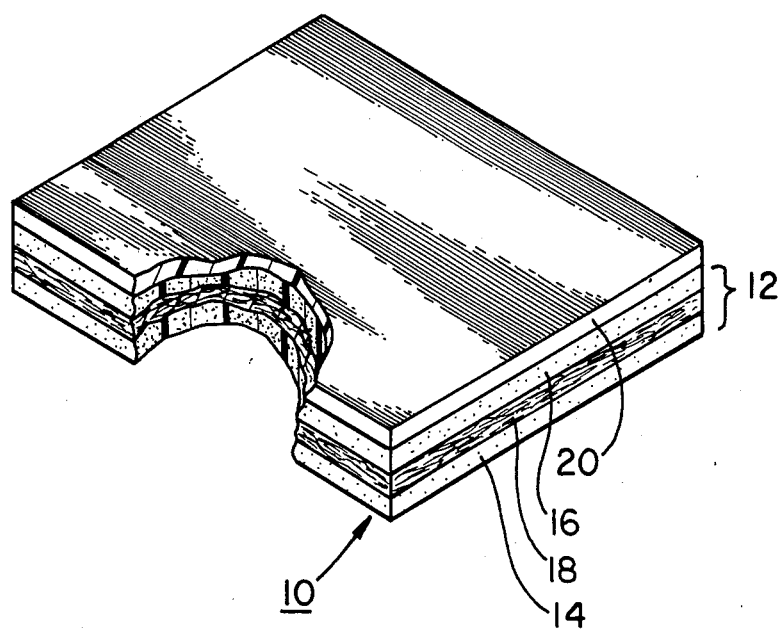

ADHESIVE STRUCTURE AND PRODUCTS INCLUDING SAME

FIELD OF THE INVENTION

This invention relates to an adhesive structure suitable for holding an article in contact with a wound area on the skin, and more particularly concerns a wound dressing including said adhesive structure.

BACKGROUND OF THE INVENTION

Various articles, e.g. tapes, films, ostomy and incontinence products and wound dressings, employ pressure sensitive adhesives which serve to hold the article in intimate contact with a fluid emitting area such as a wound. In many instances, the adhesive is used directly on the wound as well as on the surrounding normal skin. This requires that the adhesive be formulated from materials that can interact with the fluid emitted from the wound while forming a fluid-tight bond with the surrounding normal skin.

Such adhesives may typically include one or more natural or synthetic viscous or elastomeric substances, one or more water dispersible hydrocolloidal materials, and optionally a tackifier, a solvent or plasticizer and one or more water swellable cohesive strengthening agents.

For example, Chen et al. in U.S. Pat. No. 4,253,460, disclose an ostomy adhesive comprising a hydrocolloid gum, such as guar gum, locust bean gum, pectin, gum karaya and mixtures thereof; a pressure sensitive adhesive, such as natural rubber, silicone rubber, polyisobutylenes and the like; and, a cohesive strengthening agent, such as an inert natural or synthetic fibrous material, finely divided cellulose, a cross-linked dextran, a cross-linked carboxymethylcellulose, or a starch-acrylonitrile graft polymer. The cohesive strengthening agent provides that the adhesive is suitable for holding an ostomy product on the skin for an extended period of time, e.g. for a week or more.

Pawelcaak et al. in U.S. Pat. No. 4,538,603 disclose an occlusive dressing comprising a first adhesive layer which contacts the skin and wound, a semi-open cell elastic foam layer, and a film overlying said foam layer. A second more aggressive adhesive layer is interposed said first adhesive and foam to more suitably accommodate the difference in the adhesive requirements for the skin and the foam. This structure, based on a fluid-interactive adhesive, provides an excellent wound dressing which has enjoyed much commercial success in that the integrity of the structure is enhanced by the presence of the second adhesive.

By interaction of the adhesive with the emitted fluids is meant that a considerable portion of the fluids must be able to permeate through, or be absorbed into, the adhesive while the adhesive still maintains enough "wet tack" to adhere to the wound and the surrounding normal skin. As the adhesive interacts with large amount of fluids (extended time and/or heavy fluid flow), it typically becomes gel-like. Even though the designed-in "wet tack" properties maintain contact between the wound and the adhesive, the tenacity of the bond at the wound dressing/adhesive interface can be adversely affected.

Thus, since such fluid interactive materials adhere to the wound for extended periods, in many cases it is ultimately the loss of adhesion to the ostomy product, wound dressing, tape or film that necessitates replacement thereof. For example, even in the occlusive dressing of U.S. Pat. No. 4,538,603, described above, the fluids which eventually permeate the first adhesive are believed to have a deleterious effect on the second adhesive. Often it is the resulting separation of the semi-open cell foam and polyurethane film from the adhesives, and not slippage of the adhesives from the skin or wound, that makes a dressing change necessary. This is especially true for wounds emitting large amounts of fluids.

Also useful in the area of wound dressings are the calcium alginate fiber or wool dressings available as Kaltostat from Cair, Ltd. or Sorbsan from NI Medical, Ltd, known for their hemostatic capabilities. The calcium alginate wool is applied to a wound and begins to absorb wound fluids. Then, by ion exchange of some of the calcium in the wool with the sodium in the wound fluid, the dressing is rendered capable of absorbing yet larger amounts of fluid during which time the dressing takes on a gel-like consistency. The moist gel of the dressing is believed to enhance the healing process and facilitates less injurious dressing changes. A problem with these dressings, however, has been that they are air permeable and the gel can dry out and form a scab on the wound. Although these calcium alginate wools are completely biocompatible and biodegradable, the formation of the scab is thought to have a negative effect in the wound healing process. Since these wools form such a gel upon fluid absorption, adhesion of moisture impervious films thereto for the formation of occlusive dressings has proven a difficult task.

While the above-described articles and the adhesives they utilize continue to be extremely beneficial to the patient and clinician in the surgical, wound dressing, incontinence and ostomy care fields, products with an improved adhesive, particularly wound dressings, suited for use on wounds emitting large amounts of fluid would be a useful addition to the art.

SUMMARY OF THE INVENTION

In accordance with the present invention an improved adhesive structure for adhesion of an article to a fluid-emitting wound and the surrounding normal skin is disclosed. The adhesive structure comprises a first contact region comprised of a fluid-interactive adhesive material which provides adhesion to said wound and surrounding normal skin; a second contact region comprised of the same or a different adhesive material, which provides adhesion between said first region, or another region integral with said first region, and said article; and an absorbent region comprised of an absorbent fibrous, fabric or foam material intermediate the first and second regions whereby enhanced cohesion between said first and second regions and between said second region and said articles under conditions of heavy fluid emission, is provided.

DETAILED DESCRIPTION OF THE INVENTION

The present invention pertains to an improved adhesive structure which includes an absorbent region intermediatly two regions of adhesive materials. Although several of the fabrics, foams or fibers disclosed herein for use in the absorbent region are known for their use as wound dressings, the incorporation of these materials as an absorbent region sandwiched between a two-region adhesive has not been hertofore disclosed. For example, in one embodiment the material of the absorbent region can be calcium alginate wool or fiber. Since this material exists either as a fiber in the unsaturated state or a gel when saturated with fluids (such as those emitted by a wound), it was unexpected that its incorportion
that its incorporation into the present adhesive structure would enhance the cohesive properties of, for example, a multilayered wound dressing which employs such a structure. Surprisingly, an improved adhesive structure, with long lasting cohesive properties especially suited for wounds emitting large amounts of fluid, is provided.

The material of the absorbent region, for example calcium altrnate fieer, and the fluid-interactive adhesives provide a superior combination. This is because the calcium alginate far beyond that of the hydrocolloids within the adhesives, while the fluid-interactive adhesives keep the calcium alginate fiber in a moist, substantially occlusive environment thereby preventing drying out of the fiber-and wound.

In a preferred embodiment, the adhesive structure of the present invention is art of a multilayered wound dressing. One such wound dressing 10 is illustrated in FIG. 1 wherein the adhesive structure 12 includes a first contact region 14 which is comprised of an adhesive material which is pressure sensitive and fluid itteractive so that it can adhere to a fluid emitting wound as well as the normal surrounding skin. The adhesive structure 12 also includes a second contact region 16 which overlies the first contact region 14. The second contact region 16 is comprised of an adhesive material which may be the same as, or different than, that of the first contact region 14 and serves to provide cohesion between the adhesive structure 12 and the balance of the dressing 10. The adhesive structure 12 further includes an absorbent region 18 interposed and bonded to the first and second contact regions 14, 16. The absorbent region 18 may comprise a fabric, fiber, or foam chosen for its ability both to absorb fluids emitted from a wound and to be bonded to the first and second regions 14, 16. Although shown in th FIGURE as a distinct layer, the absorbent region 18 can alternatively be a region of absorbent material intermediate the first and second regions 14, 16 and impregnated with the adhesive materials thereof. Optionally, the absorbent material may be in the form of strands or particles that are dispersed throughout the first and second regions 14, 16. Overlying the adhesive structure 12, and bonded to the second contact region 16 thereof, is a backing layer 20.

The adhesive material of the first and second contact regions 14, 16 may comprise a homogeneous blend of one or more pressure sensitive adhesive materials and one or more water dispersible hydrocolloid materials. One or both of the first and second contact regions 14, 16 may also include a tackifier and a plasticizer or solvent. Additionally one or more thermoplastic elastomers may be included with the pressure sensitive adhesive material in either or both contact regions 14, 16, as well as, one or more natural or synthetic polymers capable of developing elastomeric properties when hydrated.

Suitable pressure sensitive adhesive materials for inclusion in the contact regions 14, 16 are various natural or synthetic viscous or elastomeric substances such as natural rubber, silicone rubber, polyisobutylene, etc. Low molecular weight polyisobutylenes having a viscosity average molecular weight of from about 36,000 to about 58,000 (Florey) possessing pressure sensitive adhesive properties are preferred. Such polyisobutylenes are commercially available under the trademark Vistanex from Exxon as grades LM-MS and LM-MH.

Optionally, one or more thermoplastic elastomers can be included in the pressure sensitive adhesive component of the contact regions 14, 16. These elastomers impart the properties of rubber-like extensibility and both rapid and complete recovery from modular strains to the pressure sensitive adhesive component. Suitable thermoplastic elastomers include medium molecular weight polyisobutylenes having a viscosity average molecular- weight of from about 1,150,000 to 1,600,000 (Florey), butyl rubber which is a copolymer of isobutylene with a minor amount of isoprene having a viscosity average molecular weight of from about 300,000 to about 450,000 (Florey), and styrene copolymers such as styrene-butadiene-styrene (S-B-S), styrene-isoprene-styrene (S-I-S), and styrene-tthylene/butylene-styrene (S-EB-S) which are commercially available, for example, from Shell Chemical Co. under the trademrrk Kraton as Kraton D1100, D1102, Kraton D1107, Kraton 4000, Kraton G1600, and Kraton G4600. Preferred thermoplastic elastomers are butyl rubber having a viscosity average molecular weight of about 425,000 (commercially available from Exxon as grades 077 or 065), polyisobutylene having a viscosity average molecular weight of about 1,200,000 (commercially available under the trademark Vistanex from Exxon as grade L-100), and styrene-isoprene-styrene (S-I-S) copolymers (commercially available from Shell as Kraton D1107).

The pressure sensitive adhesive component including the optional thermoplastic elastomer is present in the cowntact regions 14, 16 from about 20 percent to about 70 percent by weight of the composition, preferably from about 25 percent to about 50 percent ..y weight. The thermoplastic elastomer can be present at from about 20 percent to about three t[mes the weight of the pressure sensitive elastomeric substances.

The contact regions 14, 16 include from about 10 percent to about 65 percent by weight of one or more water dispersible hydrocolloid materials. Suitable hydrocolloid materials include sodium or calcium cabboxymethylcellulose, pectin, gelatin, guar gum, locust bean gum, collagen, gum karaya, alginic acid, calcium alginate and sodium alginate. The preferred hydrocollodd material in accordance with the present invention is sodium alginate, available in powder form, for example, as Kelset TM , a product of the Kelco Division of Merck and Company, Inc. This sodium alginate powder typically also contains some calcium (these combined calcium and sodium alginates are also referred to as alginic acid in the art). However, as used hereinafter, sodium alginate will be used to refer to sodium alginate and sodium/calcium alginate powders.

The sodium alginate powder is preferred because it compliments the preferred calcium alginate wool or fiber of the absorbent region 18. This is s because typically the absorptivity of the fibers is greater, but occurs at a slower rate, compared to the alginate powders. Thus, a rapid initial absorption of fluids is provided by the alginate powders and a slower sustained absorption is provided by the calcium alginate fibers of the absorbent region 18. Once the sodium alginate within the first and second regions 14, 16 is saturated, it serves to provide a moist, substantially occlusive environment for the calcium alginate fibers.

Preferably, the water dispersible hydrocolloids are present at from about 30 percent to about 65 percent by weight of the contact regions 14, 16.

The water dispersible hydrocolloids provide wet tack for the contact regions 14, 16 while the pressure sensitive adhesive component provides dry adhesion and imparts structural integrity to the contact regions 14, 16.

The contact regions 14, 16 may also include from about 5 percent to about 25 percent by weight of a plasticizer or solvent such as mineral oil or petrolatum with mineral oil being preferred and from about 10 percent to about 25 percent by weight of a tackifier such as a terpene resin.

Small amounts, i.e., less than 5 percent by weight of other ingredients may be included within the contact regions 14, 16. For example, an antioxidant such as butylated hydroxyanisole or butylated hydroxytoluene, a deodorant such as chlorophyllins, or a perfume agent may be included. In addition, small amounts of a pharmacologically active ingredient can be included in the first contact region 14. For example, an antibiotic or antimicrobial agent such as neomycin, an antiseptic agent such as povidone iodine, and an antiinflammatory agent such as hydrocortisone or triamcinolone acetonide.

The material of the absorbent region 18 can be a fabric, foam, fiber or the like which is capable of both absorbing fluids and bonding to the first and second contact regions 14, 16. Materials suitable for use in the absorbent region include lyophilized hydrocolloid foams, such as the gelatin and carboxymethylcellulose foams described in U.S. Pat. No. 4,292,922, sodium/calcium alginate fibers (wool), calcium alginate fibers (wool) and the like. As mentioned above, the calcium alginate fibrous material is preferred. This material is commercially available as Kaltostat from Cair, Ltd. or Sorbsan from NI Medical, Ltd. Preparation of such fibers has been described in British Pat. Nos. 653,341 and 1,394,741.

A disadvantage in the use of calcium alginate wool wound dressings in the prior art is that for reasonably rapid absorption of wound fluids the fiber size must be kept small, which in turn can significantly reduce the strength of that dressing. In the present invention, the calcium alginate fibers can be of small diameter since the adhesive sandwich formed by the first and second contact regions 14, 16 provide added strength. On the other hand, for situations where greater strength is needed and larger fibers are employed, the probability of the dressing drying out and forming a scab are greatly reduced in the present case. This is because the fluid interactive adhesives of the present structure keep the dressing nnd wound moist even if the calcium alginate fiber is slower in absorption of the wound fluids.

Referring back to the wound dressing 10 shown in the FIGURE, the backing layer 20 is shown overlying and bonded to the second contact region 16 of the adhesive structure 12. The backing layer 20 can be of a polymeric film, a fabric or a semi-open cell polymeric foam, e.g. polyurethane foam which may be covered with a polymeric film. Suitable fabrics for the backing layer include cellulose, polypropylene and a nonwoven polyester fabric available as Sontara TM from DuPont, which is preferred.

In a typical wound dressing 10, as contemplated by the present invention, the first and second contact regions 14, 16 should be at least about 0.02 cm thick and up to any convenient thickness such as 0.12 cm or more. Preferably these regions 14, 16 are between about 0.05 and 0.10 cm thick. The absorbent region 18 should be between about 0.02 and 0.10 cm thick and is preferably between about 0.02 and 0.07 cm thick. The backing layer 20 can be any convenient thickness, e.g. between abou 0.002 and 0.06 cm thick.

In accordance with the present invention, a preferred wound dressing includes the first and second regions comprising about 10 percent by weight of low molecular weight polyisobutylene, about 21 percent by weight of a styrene-isoprene-styrene copolymer, about 20 percent by weight of mineral oil, about 2 percent by weight of an antioxidant, about 12 percent by weight of a tackifier, and about 35 percent by weight of sodium alginate powder; the absorbent region comprising calcium alginate fibers; and, the backing layer comprising a nonwoven polyester fabric, e.g. Sontara TM available from DuPont.

Optionally, the adhesive structure 12 of the FIGURE may serve as a wound dressing without any additional layers or regions.

Additionally, the present invention contemplates employing the adhesive structure 12 of the FIGURE in conjunction with any article where adhesion of the article to areas of heavy fluid emission is required. Therefore, instead of the backing layer 20, other articles such as surgical tape backings or films, ostomy products, incontinence products and the like may overlie and be bonded to the adhesive structure 12. The resulting products have excellent adhesion to, for example, wounds emitting large amounts of fluid and also possess superior cohesion even after absorption of large amounts of these emitted fluids.

The adhesive structure 12 of the present invention can be prepared as follows. First to make the adhesive material for the first and second contact regions, a homogeneous dispersion of the pressure sensitive adhesive and any thermoplastic elastomer is prepared with a heavy duty mixer, e.g., a kneader mixer or sigma blade mixer. The hydrocolloid gums, water swellable cohesive strengthening agents, hydratable polymers, or any other optional ingredients are added and mixing is continued until a homogeneous dough is formed. (In cases where thermoplastic elastomer is used, it may prove beneficial to separately mix, and thereby breakdown, this component separately before mixing with the other components.) The so-formed dough is then extruded into a thick slab which is thinned down by pressure rollers to the desired thickness.

A layer of the desired thickness of the adhesive material of the second contact region 16 can be pressed with a laminate of the desired backing layer 20.

A laminate of the material comprising the fibrous region 18 is sandwiched between a desired thickness of the adhesive material of the first contact region 14 and the surface of the second region 16 opposite the backing layer 20. The so-positioned layers are then pressed together with heat to form the dressing 10.

As is known in the art, a silicone release paper can be applied to the exposed surface of the first region 14 and the dressing 10 can be cut to the desired shape and packaged. After packaging, the dressing can be sterilized, for example by gamma irradiations.

The present invention will now be described by reference to the following Example, however, it should not be limited to the details described therein.

EXAMPLE 1

A dressing was prepared having the following composition:

| Ingredient | Percent by weight |
|---|---|
| First and second regions 14,16 | |
| Polyisobutylene (Vistanex LM-MH) | 9.62 |
| Styrene-isoprene-styrene copolymer (Kraton 1107) | 20.53 |
| Na/Ca alginate (Alginic acid) Kelset powder | 35.03 |
| Mineral oil | 20.44 |
| Pentalyn H (tackifier) | 12.84 |
| Irganox 1010 (antioxidant) | 1.54 |
| Absorbent region | |
| Calcium alginate wool (Kaltostat) | |
| Backing Layer | |
| Nonwoven polyester fabric (Sontara) | |

The mineral oil (204.4 g), polyisobutylene (96.2 g), Kraton 1107 (205.3 g), and Irganox 1010 (15.4 g) were combined in a sigma blade mixer with heating (to about 115° C.) and agitating for approximately 1.5 hours. The mixture was cooled to about 100° C. and after another 30 minutes of blending, the Kelset powder (350.3 g) and the Pentalyn H (128.4 g) were added. Mixing was continued at about 100° C. for 30 minutes until a homogeneous mass was obtained.

This mass was allowed to cool and was then flattened to a thickness of about 0.05 cm. Silicon release paper was applied to both sides.

One piece of release paper was removed from each of two srips of the so-formed adhesive. A 0.03 cm thick piece of Kaltostat Wool was placed over the exposed surface of one of the strips and the exposed surface of the second adhesive strip was placed over the wool. This three layer structure was placed into an oven and heated at about 110° C. for about 5 minutes. The structure was then pressed through rollers with about a 0.10 cm spacing.

Thereafter, a backing layer of the Sontara ™ fabric was placed over the second exposed surface (second piece of release paper removed) of the second adhesive strip and pressed in place with heat supplied (about 50° C.). The resulting dressing was cut into the desired shape, packaged and sterilized.

EXAMPLES 2-13

Following the procedure of Example 1 but employing the following ingredients on a weight percent basis for the first and second contact regions 14, 16, other dressings within the scope of the invention are obtained.

| Ingredient | 2 | 3 | 4 | 5 | 6 | 7 | 8 | 9 | 10 | 11 | 12 | 13 |
|---|---|---|---|---|---|---|---|---|---|---|---|---|
| Styrene-isoprene-styrene copolymer (Kraton 1107) | 6 | — | — | — | 6.75 | 20 | 6 | — | — | — | 6.75 | 10 |
| Polyisobutylene (Vistanex LM-MH) | 8 | 40 | 20 | 15 | 8 | 10 | 8 | 40 | 20 | 15 | 8 | 20 |
| Polyisobutylene (Vistanex 100) | — | — | 25 | — | — | — | — | — | 25 | — | — | — |
| Sodium Carboxymethylcellulose | 15 | 20 | 35 | 15 | 14.34 | 15 | 10 | — | — | — | — | — |
| Guar Gum | — | — | 20 | 20 | — | 20 | — | — | — | — | — | — |
| Butyl Rubber (Grade 065) | 16.25 | — | — | — | 16.25 | — | 16.25 | — | — | — | 16.25 | — |
| Antioxidant (Irganox 1010) | 0.5 | — | — | 0.5 | 0.5 | — | 0.5 | — | — | 0.5 | 0.5 | — |
| Pectin | 15 | 20 | — | — | 14.33 | — | — | — | — | — | — | — |
| Gelatin | 15 | 20 | — | — | 14.33 | — | — | — | — | — | — | — |
| Mineral Oil | 11.5 | — | — | 9.5 | 13.5 | 20 | 11.5 | — | — | 9.5 | 13.5 | 20 |
| Tackifier (Pentalyn H) | 12.75 | — | — | 20 | 12 | 15 | 12.75 | — | — | 20 | 12 | 15 |
| Butyl Rubber (Grade 077) | — | — | — | 20 | — | — | — | — | — | 20 | — | — |
| Sodium Alginate (Kelset Powder) | — | — | — | — | — | — | 35 | 60 | 55 | 35 | 45 | 35 |

What is claimed is:

1. An adhesive structure, suitable for use as a wound dressing or for adhesion of an article to fluid emitting wounds and surrounding normal skin, including;
    a first contact region comprised of a fluid-interactive adhesive material which provides adhesion to said wound and surrounding normal skin;
    a second contact region comprised of the same or a different adhesive material, which provides adhesion between said first region, or another region integral with said first region, and said article; and,
    an absorbent region comprised of an absorbent material from the group consisting of sodium calcium alginate wool or fibers and calcium alginate wool or fibers interposed said first and second contact regions whereby enhanced adhesion between said first and second contact regions and between said second contact region and said article, under conditions of heavy fluid emission, is provided.

2. The structure of claim 1 wherein the adhesive materials of the first and second regions comprise a blend of one or more pressure sensitive adhesives, and, one or more water dispersible hydrocolloids.

3. The structure of claim 2 wherein said pressure sensitive adhesives comprise one or more elastomeric materials selected from the group consisting of natural rubber, silicone rubber, and low molecular weight polyisobutylenes and optionally one or more thermoplastic elastomers selected from the group consisting of medium molecular weight polyisobutylenes, butyl rubber, and styrene compolymers.

4. The structure of claim 3 wherein said water dispersible hydrocolloids are selected from the group consisting of guar gum, sodium carboxymethylcellulose, calcium carboxymethylcellulose, pectin, gelatin, locust bean gum, collagen, gum karaya, alginic acid, calcium alginate, and sodium alginate.

5. The structure of claim 4 wherein said adhesive materials of the first and second regions further comprise one or more materials selected from the group consisting of plasticizers or solvents, tackifiers, antioxidants and pharmacologically active ingredients.

6. The structure of claim 5 wherein said adhesive materials of the first and second regions comprise between about 20 to 70 percent by weight of low molecular weight polyisobutylene and said optional thermoplastic elastomer; between about 10 and 65 percent by weight of said hydrocolloids; between about 5 and 25 percent by weight of a plasticizer or solvent; between about 10 and 25 percent by weight of a tackifier; and up to about 5 percent by weight of antioxidants and/or pharmacologically active ingredients.

7. The structure of claim 6 wherein said adhesive materials comrrise about 10 percent by weight of said polyisobutylnne, about 21 percent by weight of a thermoplastic elastomer, about 20 percent by weight of a plasticizer or solvent, about 2 percent by weight of an antioxidant, about 12 percent by weight of a tackifier, and about 35 percent by weight of a hydrocolloid.

8. The structure of claim 7 wherein said thermoplastic elastomer is a styrene-isoprene-styrene copolymer, said plasticizer or solvent is mineral oil, and said hydrocolloid is sodium alginate.

9. The structure of claim 1 wherein said absorbent region is a distinct layer interposed, and bonded to, said first and second regions.

10. The structure of claim 1 wherein said absorptive region comprises the absorbent material intermediate said first and second regions and substantially impregnated with the adhesive materials of said first and second regions.

11. The structure of claim 1 wherein said first contact region is betwee about 0.02 and 0.12 centimeters thick, said absorbent region is between about 0.02 and 0.10 centimeters thick, and said second contact region is between about 0.02 and 0.12 centimeters thick.

12. The structure of claim 1 wherein said article is selected from the group consisting of ostomy products, incontinence products, wound dressings, or surgical tapes.

13. The wound dressing of claim 1 further comprising a backing layer overlying and bonded to the second contact region of said adhesive structure.

14. The wound dressing of claim 13 wherein said backing layer comprises a material selected from the group consisting of nonwoven polyester fabric, cellulose, and polypropylene.

15. The wound dressing of claim 14 wherein said backing layer is a nonwoven polyester fabric.

16. The wound dressing of claim 13 wherein said backing layer is between about 0.002 and about 0.06 centimeters thick.

17. A multilayered wound dressing, suitable for use on wounds emitting large amounts of fluid, comprising
a first contact region being about 0.05 centimeters in thickness and comprised of about 10 percent by weight of low molecular weight polyisobutylene, about 21 percent by weight of styrene-isoprene-styrene copolymer, about 35 percent by weight of sodium alginate, about 20 percent by weight of mineral oil, about 2 percent by weight of an antioxidant and about 12 percent by weight of a tackifier, and fluid interactive providing pressure sensitive and fluid interactive providing adhesion of the balance of the dressing to the wound and surrounding skin;
an absorbent region, overlying and bonded to said first contact region, being about 0.02 centimeters in thickness and comprised of calcium alginate fibers, which absorbent region provides increased absorption of fluids emitted from said wound and enhanced cohesion to said dressing layers;
a second contact region, overlying and bonded oo said absorbent region, being about 0.05 centimeters in thickness and comprised of the same material as said first region, which second region provides cohesion between said absorbent region and the balance of the dressing; and,
a backing layer, overlying and bonded to said second contact region, being about 0.02 centimeters in thickness and comprised of a nonwoven polyester fabric.

* * * * *